US009304331B2

(12) United States Patent
Carrara

(10) Patent No.: US 9,304,331 B2
(45) Date of Patent: Apr. 5, 2016

(54) EYEGLASSES WITH HIGH FLEXIBILITY IN USE

(71) Applicant: Marco Carrara, San Felice (IT)

(72) Inventor: Marco Carrara, San Felice (IT)

( * ) Notice: Subject to any disclaimer, the term of this patent is extended or adjusted under 35 U.S.C. 154(b) by 0 days.

(21) Appl. No.: 14/436,542

(22) PCT Filed: Oct. 29, 2013

(86) PCT No.: PCT/EP2013/072587
§ 371 (c)(1),
(2) Date: Apr. 17, 2015

(87) PCT Pub. No.: WO2014/075914
PCT Pub. Date: May 22, 2014

(65) Prior Publication Data
US 2015/0248025 A1 Sep. 3, 2015

(30) Foreign Application Priority Data

Nov. 16, 2012 (IT) ................. MI2012A1957

(51) Int. Cl.
*G02C 1/00* (2006.01)
*G02C 11/00* (2006.01)
*A61B 5/024* (2006.01)
*A61B 5/00* (2006.01)
*G02C 3/00* (2006.01)
*G02C 5/00* (2006.01)

(52) U.S. Cl.
CPC ............ *G02C 11/10* (2013.01); *A61B 5/02427* (2013.01); *A61B 5/02438* (2013.01); *A61B 5/6803* (2013.01); *A61B 5/6814* (2013.01); *G02C 3/003* (2013.01); *G02C 5/001* (2013.01); *A61B 5/6821* (2013.01); *A61B 2560/0214* (2013.01); *A61B 2560/0462* (2013.01)

(58) Field of Classification Search
CPC .................................. G02C 11/10; G02C 5/14
USPC .............................. 351/158, 41, 121; 600/500
See application file for complete search history.

(56) References Cited

U.S. PATENT DOCUMENTS

| 5,585,871 A | 12/1996 | Linden |
| 6,431,705 B1 * | 8/2002 | Linden ................... G02C 11/00 351/158 |
| 2003/0018274 A1 | 1/2003 | Takahashi et al. |

(Continued)

FOREIGN PATENT DOCUMENTS

| DE | 3106315 | 9/1982 |
| IT | MI20101083 | 12/2011 |

OTHER PUBLICATIONS

International Search Report dated Jan. 23, 2014; International Application No. PCT/EP2013/072587; International Filing Date: Oct. 29, 2013; 4 pages.

(Continued)

*Primary Examiner* — Hung Dang
(74) *Attorney, Agent, or Firm* — Blank Rome LLP

(57) ABSTRACT

The eyeglasses (1) with high flexibility in use comprise a system for measuring the wearer's heart rate, the measuring system comprising a microcontroller (11), at least one heart rate sensor (12), means (13) for generating a visual and/or audible signal correlated to the measured heart rate, and an autonomous electrical power source (14), the measuring system further comprising adjustable means for positioning the sensor (12) against an anatomical area suitable for measuring the heart rate.

13 Claims, 5 Drawing Sheets

(56) References Cited

U.S. PATENT DOCUMENTS

| | | |
|---|---|---|
| 2007/0109491 A1 | 5/2007 | Howell et al. |
| 2009/0059159 A1* | 3/2009 | Howell .................. G02C 11/00 351/41 |
| 2012/0029367 A1 | 2/2012 | Hobeika |

OTHER PUBLICATIONS

Written Opinion dated Jan. 23, 2014; International Application No. PCT/EP2013/072587; International Filing Date: Oct. 29, 2013; 7 pages.

English abstract; German Application No. DE3106315; Feb. 16, 1981; 1 page.

* cited by examiner

EYEGLASSES WITH HIGH FLEXIBILITY IN USE

FIELD OF USE

Background of the Invention

The present invention relates to eyeglasses with high flexibility in use. It is very important to monitor at least some of the main vital parameters of a person, especially during prolonged physical exertion, since an anomaly thereof may be symptomatic of a dysfunction or pathology affecting the coronary and/or cardiovascular systems, and/or the circulatory system more in general.

Some of these pathologies are silent and asymptomatic and only an early, timely diagnosis can help prevent the worst, which sometimes means the occurrence of permanent damage and sometimes even death.

Several types of eyeglasses are known which have high flexibility in use and a system for measuring the heart rate.

The measuring system comprises a microcontroller, connected to which there is at least one heart rate sensor and a device for displaying the measured heart rate.

In many of the known solutions, the heart rate measuring system is not completely integrated within the eyeglasses, the consequence being that some of the functional parts thereof are distributed in other accessories that must be worn separately from the eyeglasses, for example electrodes to be applied on the skin or electrical power supply units to be attached to a belt.

Such solutions can thus prove cumbersome, uncomfortable and impractical for the wearer.

An optimal acquisition of the signal requires correctly positioning the sensor and stably maintaining the correct position of the sensor. The current position of the sensor depends, however, on different variables, including the specific anatomical conformation of the wearer's head and the type of activity engaged in while wearing the eyeglasses, since in the case of a physical activity of a certain entity, the sensor is subjected to vibrations and oscillations which may also be intense and move it from the area suitable for picking up the signal.

Any movements of the sensor from the optimal sensing position generate disturbances in the acquired signal which can significantly affect the measurement. Under these conditions, therefore, it is not possible to ensure either the accuracy or repeatability of the measurement itself.

In other known solutions, the inclusion of a measuring system limits the possibility of personalizing the eyeglasses in order to satisfy changed technical or aesthetic needs of the wearer. This occurs in particular because the components of the measuring system are located on all functional parts of the eyeglasses, from the frame to the lenses.

SUMMARY OF THE INVENTION

The technical task, the present invention sets itself is thus to provide eyeglasses that, have a compact, lightweight construction, are comfortable and practical to wear and capable of integrating different functions so as also to ensure monitoring of the wearers heart rate.

Another object of the invention, is to realize eyeglasses with high flexibility in use which enable an accurate, precise and repeatable measurement of the heart rate irrespective of the anatomical conformation of the wearer's head and the type of activity engaged in by the satire while wearing the eyeglasses.

Yet another object of the invention is to provide eyeglasses which, besides having the above-described features, can be easily personalized by the wearer in order to satisfy changed technical or aesthetic needs. The technical task, as well as these and other objects are achieved, according to the present invention, with eyeglasses having high flexibility in use comprising a system for measuring the wearers heart rate, said measuring system comprising a microcontroller, at least one heart rate sensor, means for generating a visual and/or audible signal correlated to the measured heart rate, and an autonomous electrical power source, characterized in that said measuring system further comprises adjustable means for positioning said at least one sensor against an anatomical area suitable for measuring the heart rate, said adjustable means comprising at least one elastically flexible support element for said at least one sensor, said support element being supported by a temple piece of the frame from the inner side of said temple piece and being configured to bend toward the inner side of said temple piece so as to generate a force of contact of the sensor against said anatomical area which is of an entity at least sufficient to prevent the sensor from moving relative to said anatomical area at least during a heart rate measurement.

The positioning means are advantageously configured and disposed in such a way as not only to adapt the sensors position so as to position it against a anatomical area suitable tor measuring the heart rate irrespective of the anatomical conformation of the wearer's head, but also to maintain the sensor solidly attached to the sensing area it is positioned against irrespective of the type of activity engaged in by the wearer while wearing the eyeglasses.

The positioning means advantageously provide, in fact, an anchorage that keeps the eyeglasses firmly in place when the wearer makes sudden movements or takes on particular postures with his/her head.

The eyeglasses thus provide a precise and repeatable measurement, given that the signal is always picked up from the same anatomical sensing area irrespective of the anatomical conformation of the wearer's head and the type of activity the wearer is engaging in while wearing the eyeglasses.

The heart rate measurement technique for the application concerned can be based on an electrical optical or mechanical/acoustic method.

The preferred, but not exclusive, measurement technique is based on an optical method.

In a preferred embodiment preferably adoptable in combination with a measurement technique based on an optical method, the positioning means comprise a support element for the sensor, having an elastically flexible body. In this case, when the eyeglasses are worn, the elastic bending of the support element, induced by the pressure exerted by the anatomical area of the wearer intended to measure the heart rate, generates a force of contact of the sensor against said anatomical area which is of an entity at least sufficient to prevent a movement of the sensor from said anatomical area.

If the sensor is of an optical type, it is possible to adjust the sensor's position by placing it precisely and stably against a vein or artery which, depending on the specific application, can be a nasal vein or artery, a temporal vein or artery or an auricular vein or artery.

Preferably, to improve the wearability of the eyeglasses, means for adjusting the rigidity of the support element are also provided.

A further particularly advantageous aspect of the invention consists in the fact that the measuring system is preferably joined solely to the frame of the eyeglasses, meaning that it does not involve the lenses of the eyeglasses.

Practically speaking, in this case there is no reciprocal constraint of either a constructive or functional character between the measuring system and the lenses in the frame, which can thus be removed and replaced independently of all the remaining functional parts of the eyeglasses.

The wearer thus has the option of changing the lenses, so as to replace them with others that differ only aesthetically (sunglass, coloured, mirror lenses, etc.) or with other technically different ones, for example because of an evolution in an optical defect of the wearer.

BRIEF DESCRIPTION OF THE DRAWINGS

Additional features and advantages of the invention will be more apparent from the description of a preferred, but not exclusive, embodiment of the eyeglasses with high flexibility in use according to the invention, given by way of illustration and not by way of limitation with reference to the appended drawings, in which.

DETAILED DESCRIPTION OF THE INVENTION

Figure 1:
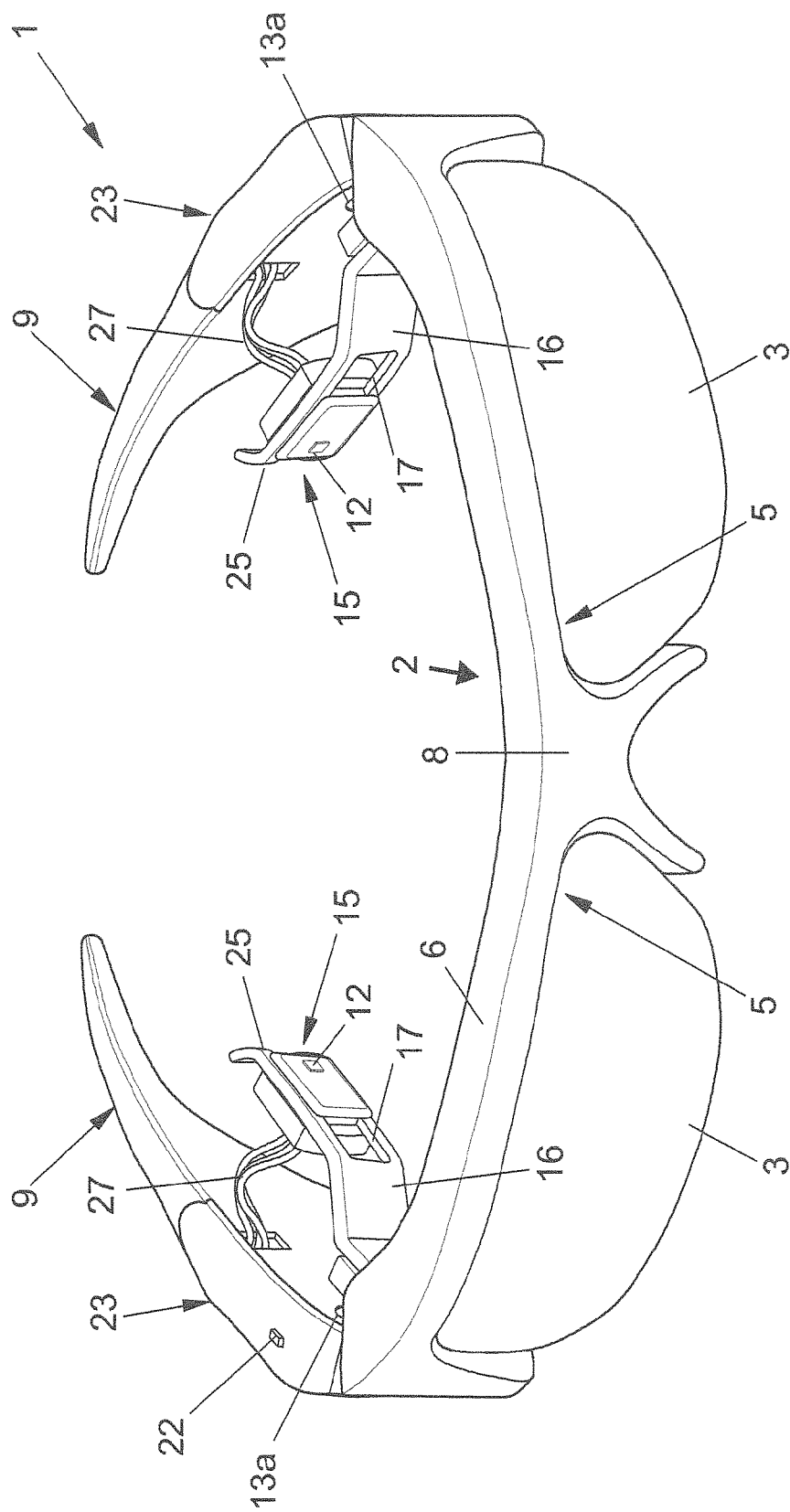
FIG. 1 shows a front perspective view of the eyeglasses.
Figure 2:
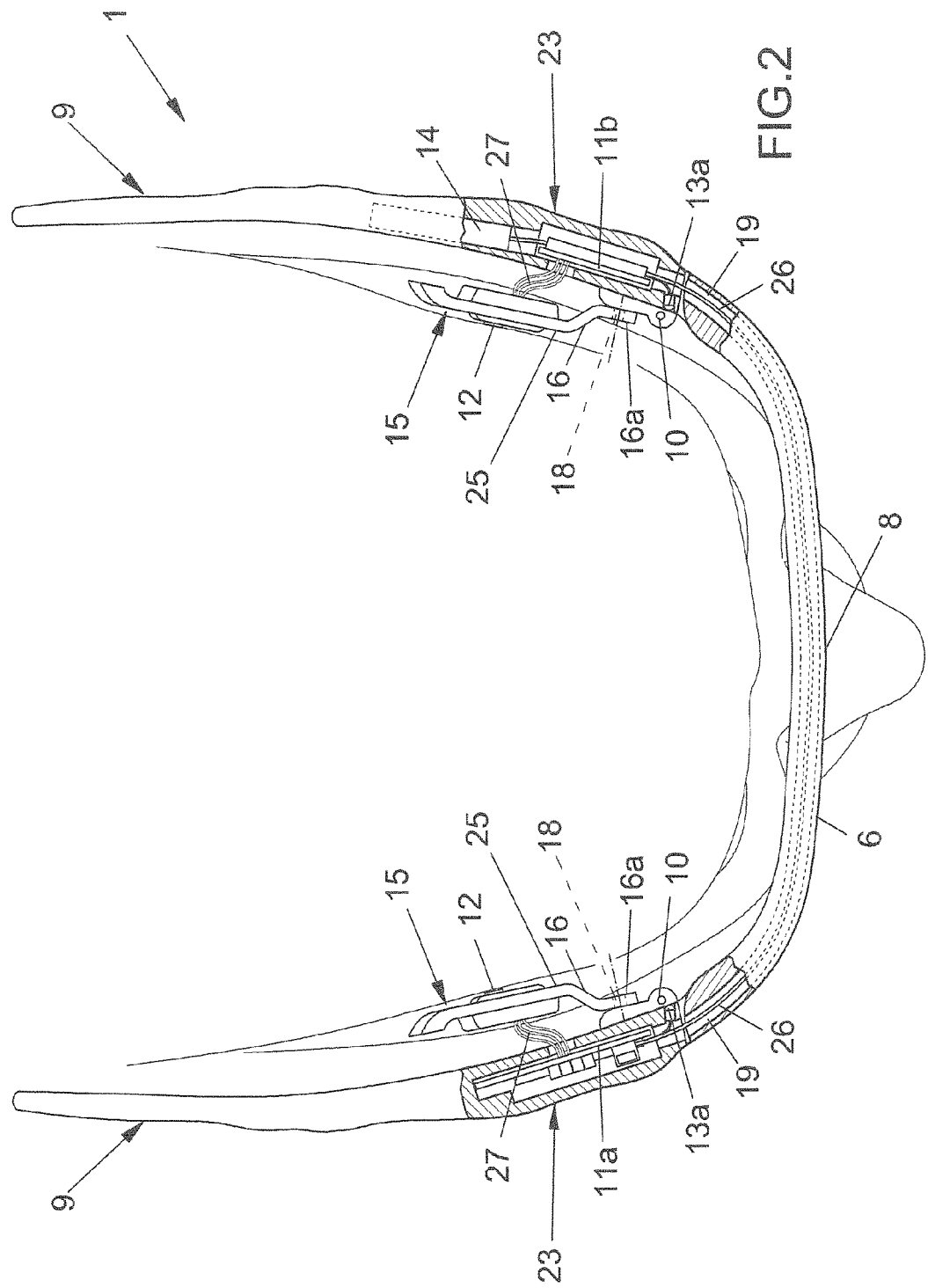
FIG. 2 shows a plan view from above of tire eyeglasses on the wearer, with a section of the frame in the zones where the temple pieces are hinged to the front piece.
Figure 3:
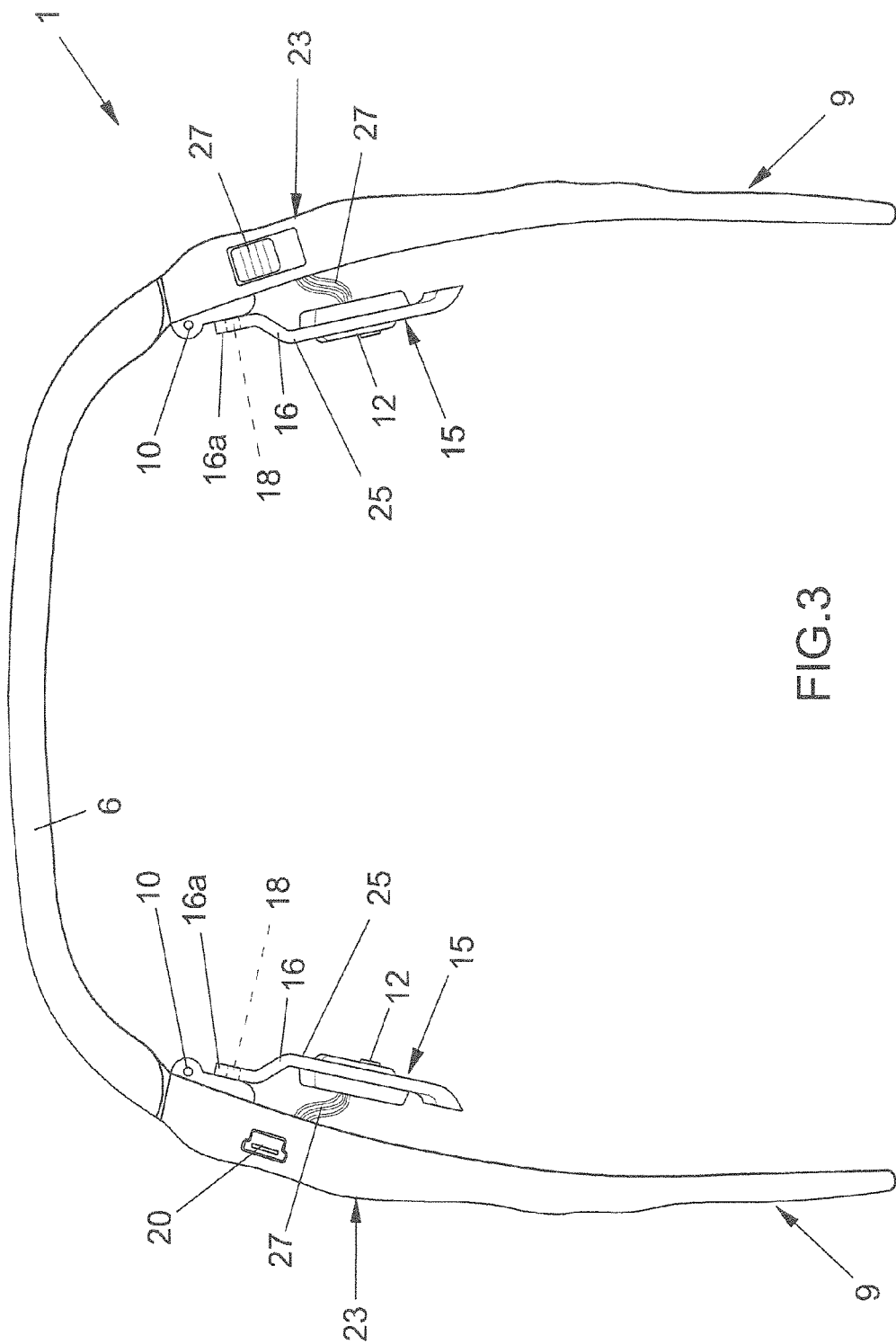
FIG. 3 shows a plan view from above of the eyeglasses.
Figure 4:
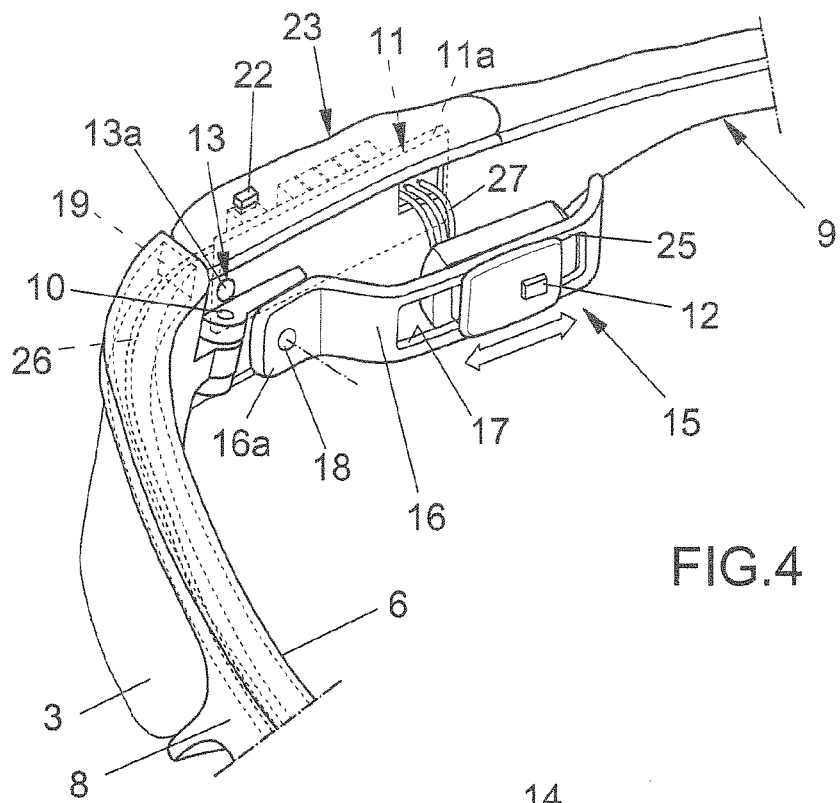
FIG. 4 shows a detailed view of the frame in the zone where the right temple piece is hinged to the front piece of the frame, and in which an arrow illustrates the translation direction for adjusting the linear position of the sensor along the support element.
Figure 5:
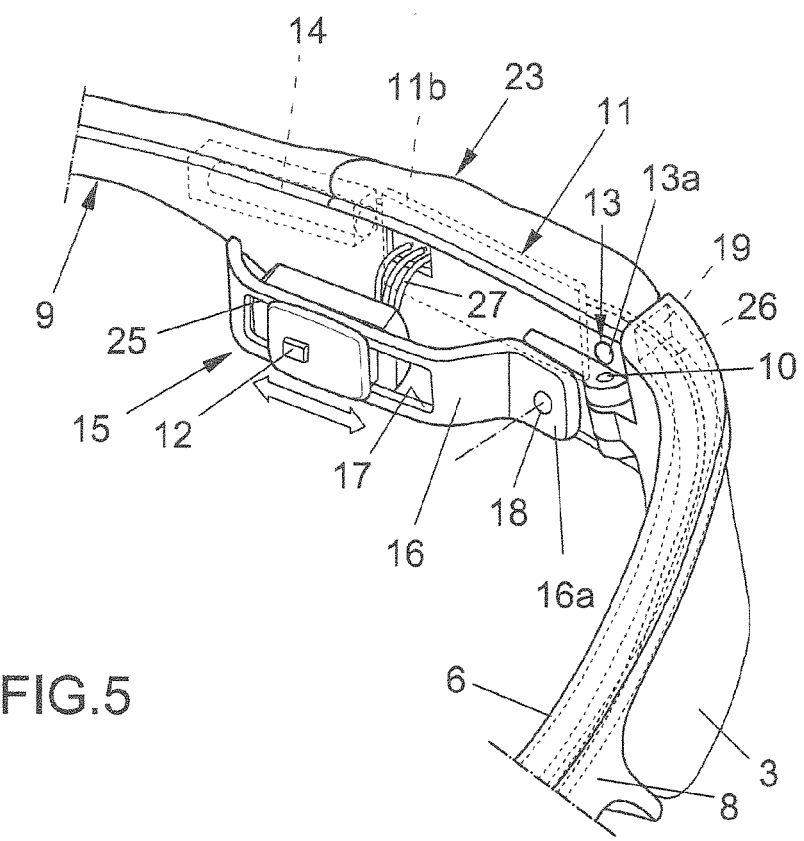
FIG. 5 shows a detailed view of the frame in the zone where the left temple piece is hinged to the front piece of the frame, and in which an arrow illustrates the translation direction for adjusting the linear position of the sensor along the support element.
Figure 6:
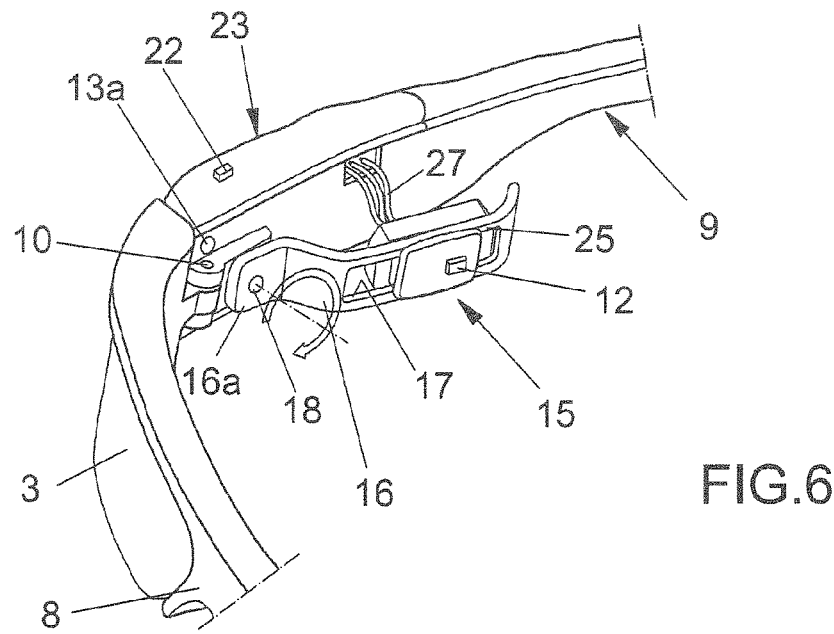
FIGS. 6 and 7 show a detailed view of the frame in the zone where the right temple piece is hinged to the front piece of the frame, and in which an arrow illustrates the adjustment of the angular position of the support element of the sensor.
Figure 7:
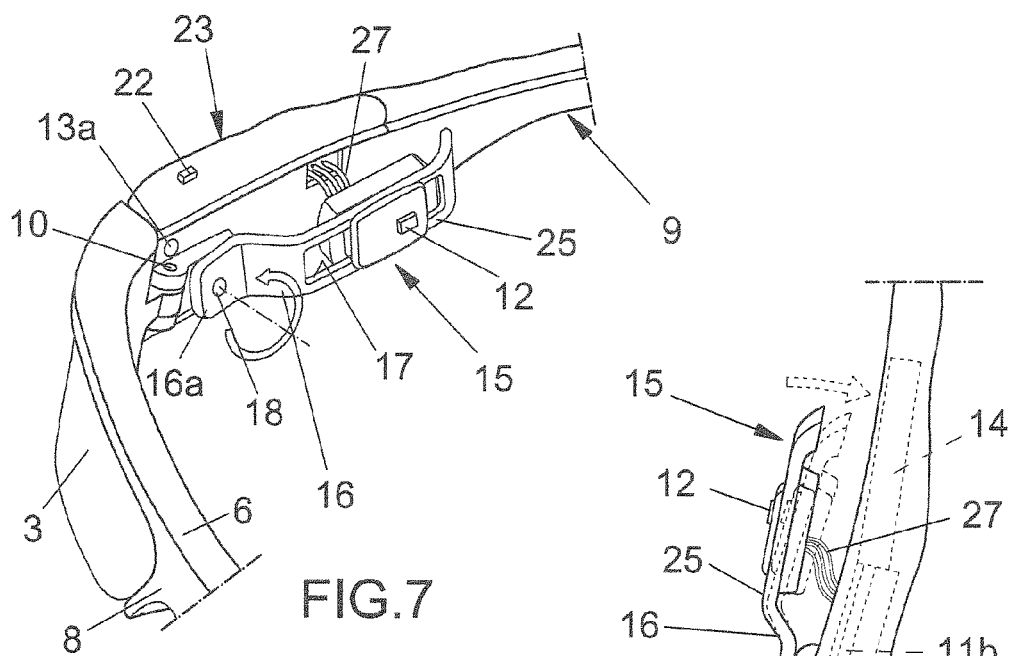
Figure 8:
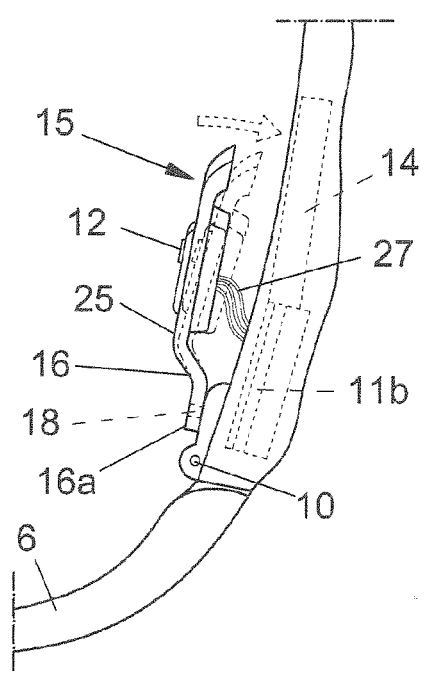
FIG. 8 shows a detailed view of the frame in the zone where the left temple piece is hinged to the front piece of the frame, and in which an arrow illustrates the bending to which the support element of the sensor can be subjected, the support element being shown with a solid line in a rest position and with a dashed line in a bent position assumed when the eyeglasses are worn.

With reference to the cited figure, eyeglasses are illustrated which are indicated overall with the reference number 1.

The eyeglasses comprise, in a known manner, a frame 2 and two lenses 3.

The frame 2 has a front piece 5 with two open circles 6, a bridge 8 connecting between the circles 6, and temple pieces 9.

In this case, the frame 2 includes the temple pieces 9 as distinct and separate elements connected by a respective hinge 10 to the front piece 5.

In further embodiments, not shown, a single lens 3 can be provided and the frame 2 can be designed so that its various parts are made in one piece, for example, the sides and front can be made in one piece, and/or the circles of the front piece can be closed or open and have, in particular, only a lower arch, etc.

For the reasons we shall see below, in the specific embodiment of the invention described, the temple pieces 9 preferably have a box-like enlargement 23 in the portion thereof proximal to the front piece 5 of the frame 2.

The lenses 3 of the eyeglasses 1 can be corrective or sunglass lenses or even neutral, i.e. simply aesthetic.

The eyeglasses 1 feature a system for measuring the wearers heart rate, comprising a microcontroller 11, at least one heart rate sensor 12, means 13 for generating a visual and/or audible signal correlated to the measured heart rate, and an autonomous electrical power source 14, typically a battery.

The optical sensor 12 is preferably-optical and employs the optical transduction technique of photoplethysmography, based on the analysis of variations in a luminous flow that crosses a microvascular bed and is proportional to the blood volume pulse in that tissue. The optical sensor 12 thus has a pair of devices: an electric-light signal converter, used as an emitter of luminous radiation (for example, a LED); and a light-electric signal converter, used as a receiver of luminous radiation (for example, a photodiode or a phototransistor). In order to monitor the blood volume pulse, the pair of devices exploits the principle of light beam reflection. The variation in blood volume at every heartbeat determines a variation in the amount of photons absorbed. By way of example, the LED emitter of the sensor 12 has an emission spectrum centered around 950 nm, whereas the phototransistor receiver of the sensor 12 is sensitive to wavelengths ranging between 700 nm and 1200 nm.

The microcontroller 11 amplifies and processes signals coming from all of the sensors 12 provided; it extracts heart rate data averaged over a given time window, and processes them according to appropriate algorithms so as to generate information to be sent to the means 13.

The microcontroller 11, which for ergonomic reasons is composed of two distinct electronic cards 11a and 11b, thus has a part interfacing with all the sensors 12 provided, a data processing part, and a part interfacing with the means 13. Connected to the microcontroller 11 there is preferably also one interface port 20 with an external electronic device (not shown, for example a USB port).

The means 13, if they are for generating a visual signal correlated with the measured heart rate, preferably comprise one or more LEDs 13a, whereas if they are for generating an audible signal correlated with the measured heart rate they preferably comprise one or more buzzers (not shown).

Naturally, in possible variants of the invention the means 13 can also comprise devices other than the ones mentioned above, for example a display, in addition to or in place of them.

The measuring system also comprises an ON pushbutton 22 and possibly other programming pushbuttons (not shown) for setting personalized lower threshold and upper threshold heart rate values based on which the means 13 must be controlled.

If no programming pushbuttons are provided, the threshold values are preset. The measuring system further comprises, advantageously, adjustable means for stably positioning the sensor 12 against a given anatomical area for measuring the heart rate.

The positioning means comprise in particular at least one support element 15 for the sensor 12.

The support element 15 has an elastically flexible body that preferably extends along a longitudinal axis.

With reference to the specific application described, the signal is picked up from a temporal vein or artery, and conveniently the support element 15 is associated with, for example hinged to, a temple piece 9 of the frame 2.

The support element 15 is formed in particular by a longitudinal plate 16 which includes at least one longitudinal section 25 and which, at the longitudinal end 16a proximal to the front piece 5 of the frame 2, is hinged by means of a pin 18 to the temple piece 9 and disposed with its main face turned at a close distance toward the inner face of the box-like portion 23 of the temple piece 9.

The pin 18 is oriented in such a way as to enable an oscillation of the plate 16 in the plane in which it mainly lies, substantially parallel to the inner face of the box-like portion 23 of the temple piece 9.

The sensor 12 is supported along a translation guide 17 fashioned from the body of the support element 15.

More precisely, the translation guide 17 extends in the longitudinal direction of the support element 15.

Fine adjustment of the angular and linear position of the sensor 12 can be achieved by providing a friction coupling between the support element 15 and the temple piece 9 via the pin 18, and a friction coupling between the sensor 12 and the support element 15 via the translation guide 17. Practically speaking, for a fine adjustment of the angular position of the sensor 12 it is sufficient to manually exert a rotation force on the support element 15 which is greater than the force of friction which maintains the support element 15 solidly attached to the temple piece 9, whereas for the fine adjustment of the linear position of the sensor 12 it is sufficient to manually exert on the sensor 12 a translation force which is greater than the friction force which maintains the sensor 12 solidly attached to the support element 15.

Naturally, an adjustment that exploits a principle other than friction is equally possible, for example one based on a selective engagement between snap-fitting teeth provided between the two coupled parts.

Once the sensor 12 has been positioned against the anatomical sensing area, the elastic bending to which the support element 15 is subjected due to interference with the wearer's head generates the contact force necessary to maintain the sensor 12 solidly attached to the anatomical sensing area in any situation, irrespective of whether the wearer is inactive or is engaging in physical activity of a certain intensity.

In this regard, to improve the wearability and comfort of the eyeglasses it is also possible to provide means for adjusting the rigidity of the support element 15. Such adjustment means (not shown in the example described) can comprise any element suitable for modifying the length of the section of the support element 15 that is active for the elastic bending.

Preferably, as shown, there is provided at least a second sensor 12 borne by a second support element 15 associated with the opposite temple piece 9.

The second support element 15 is preferably constructively and functionally equal to the one previously described.

The second sensor 12 is also preferably constructively and functionally equal to the one previously described.

Naturally, the configuration and positioning of the support element 15 of the sensor 12 can vary according to the anatomical area chosen for picking up the signal.

In the case just illustrated, the support element 15 is in a forward position along the temple piece 9 so as to position the sensor 12 substantially against the temple.

If it is preferred, however, to pick up the signal from the posterior auricular vein or artery, the support element 15 would again be associated with the temple piece 9 of the frame 2, but in a decidedly more rearward position than the one assumed in order to pick up the signal from the surface temporal vein or artery; in this case, in fact, the sensor 12, when the wearer is wearing the eyeglasses, must substantially be positioned behind the auricle.

Should one prefer instead to pick up the signal from the angular vein or artery, the support element would be associated with the front piece of the frame, in the area where it rests upon the nose.

The measuring system is advantageously entirely joined only to the frame 2. The autonomous electrical source 14 and microcontroller 11 are recess mounted in specific housings provided in the frame 2, and in particular in the enlarged box-like portion 23 of the temple pieces 9.

The means 13 for generating a visual signal are in turn integrated into the box-like portion 23 of the temple pieces 9, whereas the means 13 for generating an audible signal are located at the end of the temple pieces 9 which is distal from the front piece 5 of the frame 2.

The electric wires 26 for connecting the autonomous power source 14 to the microcontroller 11 extend along the temple pieces 9, the bridge 8 and the upper arch portion of the circles 6 of the front piece 5 of the frame 2.

In particular, the frame 2 has a duct 19 for the passage of electric wires 26.

The electric wires 27 for connecting the sensor 12 to the microcontroller 11 can instead extend in the space comprised between the support element 15 and the inner face of the enlarged box-like portion 23 of the temple piece 9.

The ON pushbutton 22 and other programming pushbuttons, where provided, are preferably mounted on the enlarged box-like portion 23 of the temple pieces 9, as is the interface port 20.

The components of the measuring system are distributed in the frame 2 in such a way as to obtain a substantial balance of weights between the right half part and left half part of the frame 2 itself.

The lenses are thus excluded from any constructive or if functional connection with the measuring system, so that they can be replaced as desired, without having to act upon the measuring system itself in any way.

The functioning of the eyeglasses according to the invention appears evident from what has been described and illustrated and, in particular, is substantially as follows.

During physical activity, all of the sensors 12 provided send the microcontroller 11 signals related to the measured heart rate.

In the case of two sensors 12, the microcontroller 11 will determine the heart rate value as the average of the measured values. This enables a more precise evaluation of the heart rate.

The microcontroller 11 processes a control signal for every LED 13a and a control signal for every buzzer, where present.

The control signal of the LED 13a is preferably intended to select a colour of the luminous pulses: for example, if the measured heart rate is below the lower threshold the control signal will activate a green LED 13a, if the measured heart rate is between the lower threshold and upper threshold, the control signal will activate a yellow LED 13a, and if the measured heart rate is above the upper threshold the control signal will activate a red LED 13a.

As far as the buzzer is concerned, the control signal is capable of modifying the frequency and/or length and/or intensity of the emitted sounds.

It has been ascertained, in practice, that the eyeglasses according to the invention are particularly advantageous due to the fact of incorporating an extremely reliable and precise system for monitoring the wearer's heart rate.

The eyeglasses thus conceived are susceptible of numerous modifications and variants, all falling within the scope of the inventive concept; moreover, all the details may be replaced with technically equivalent elements.

In practical terms, the materials used as well as the dimensions, can be any whatsoever according to need and the prior art.

The invention claimed is:

1. Eyeglasses with high flexibility in use comprising a system for measuring a heart rate of a wearer, said system comprising:
a microcontroller,
at least one heart sensor,
means for generating a visual or audible signal correlated to the measured heart rate,
an autonomous electrical power source, and
adjustable means for positioning said at least one heart sensor against an anatomical area suitable for measuring the heart rate, said adjustable means comprising at least one elastically flexible support element for said at least one heart sensor, said support element being supported by a temple piece of a frame of the eyeglasses from and inner side of said temple piece and being configured to bend toward the inner side of said temple piece so as to generate a force of contact of the at least one heart sensor against said anatomical area which is of an entity at least sufficient to prevent the at least one heart sensor from moving relative to said anatomical area at least during a heart rate measurement.

2. The eyeglasses according to claim 1, wherein said measuring system is joined solely to the frame of said eyeglasses.

3. The eyeglasses according to claim 1, further comprising means for adjusting the rigidity of said support element.

4. The eyeglasses according to claim 1, wherein said at least one heart sensor is slidingly supported by said support.

5. The eyeglasses according to claim 1, wherein said at least one sensor is of the optical type.

6. The eyeglasses according to claim 1, wherein said support element is engaged by means of a hinge to said temple piece of the frame.

7. The eyeglasses according to claim 1, wherein said support element is formed by a longitudinal plate having at least a flat longitudinal section.

8. The eyeglasses according to claim 1, wherein said at least one sensor is supported along a translation guide fashioned from a body of said support element.

9. The eyeglasses according to claim 8, wherein said translation guide extends in a longitudinal direction of said support element.

10. The eyeglasses according to claim 1, wherein the at least one heart sensor comprises at least one sensor for each temple piece of the frame.

11. The eyeglasses according to claim 1, further comprising electrical wiring for connecting the autonomous electrical power source to the microcontroller, wherein the electrical wiring extends along an internal groove of said frame.

12. The eyeglasses according to claim 1, further comprising at least one interface port connected to the microcontroller, the at least one interface port for interfacing with an external electronic device.

13. The eyeglasses according to claim 12, wherein said at least one interface port is provided in a temple piece of the frame.

* * * * *